US011976093B2

United States Patent
Zou et al.

(10) Patent No.: US 11,976,093 B2
(45) Date of Patent: May 7, 2024

(54) ULTRASONIC-ASSISTED PRETREATMENT METHOD FOR EXTRACTION OF MULTIPLE STEROID HORMONES IN SEDIMENT

(71) Applicant: Jiangnan University, Wuxi (CN)

(72) Inventors: Hua Zou, Wuxi (CN); Xin Luo, Wuxi (CN); Ruihua Dai, Wuxi (CN); Yun Zhang, Wuxi (CN); Shu Shu, Wuxi (CN); Zhengkai Zhou, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 692 days.

(21) Appl. No.: 17/170,969

(22) Filed: Feb. 9, 2021

(65) Prior Publication Data

US 2021/0163525 A1 Jun. 3, 2021

Related U.S. Application Data

(63) Continuation of application No. PCT/CN2020/087217, filed on Apr. 27, 2020.

(30) Foreign Application Priority Data

May 5, 2019 (CN) .......................... 201910368112.5

(51) Int. Cl.
   *B01D 11/02* (2006.01)
   *B01D 21/26* (2006.01)
   (Continued)

(52) U.S. Cl.
   CPC ........... *C07J 75/00* (2013.01); *B01D 11/0257* (2013.01); *B01D 11/0265* (2013.01);
   (Continued)

(58) Field of Classification Search
   CPC ............ B01D 11/0265; B01D 11/0284; B01D 11/0288; G01N 2030/062
   See application file for complete search history.

(56) References Cited

FOREIGN PATENT DOCUMENTS

| CN | 101813676 A | 8/2010 |
| CN | 102183606 A | 9/2011 |

(Continued)

OTHER PUBLICATIONS

Wada, Toyohito et al.—JP 2007-248442 A machine translation—Sep. 27, 2007 (Year: 2007).*

(Continued)

*Primary Examiner* — Bradley R Spies
(74) *Attorney, Agent, or Firm* — IPRO, PLLC; Na Xu

(57) ABSTRACT

The disclosure discloses an ultrasonic-assisted pretreatment method for extraction of multiple steroid hormones in a sediment, including the following steps: (1) lyophilizing the sediment, grinding the sediment, and passing the ground sediment through a 40-60-mesh sieve; (2) placing the sample obtained in step (1) in a container; (3) adding an extractant to the container in step (2), shaking the mixture for 15 s-30 s, centrifuging the mixture to collect an supernatant after ultrasonication, and repeating extraction three times; where the extractants used in the three times of extraction are two of methanol, acetonitrile and acetone; and (4) after mixing the supernatants of the three times of extraction obtained in step (3), concentrating the mixture under a nitrogen flow at 20-30° C., passing the concentrated mixture through a filter, and performing detection. By using the method of the disclosure, the maximum recovery can be up to 100%. The application range is wide, and a recovery of the plurality of steroid hormones each can be up to 73% or above.

13 Claims, 2 Drawing Sheets

(51) Int. Cl.
*C07J 75/00* (2006.01)
*G01N 30/06* (2006.01)
*C07J 1/00* (2006.01)
*C07J 7/00* (2006.01)

(52) U.S. Cl.
CPC ........ *B01D 11/028* (2013.01); *B01D 11/0284* (2013.01); *B01D 11/0288* (2013.01); *B01D 21/262* (2013.01); *G01N 30/06* (2013.01); *C07J 1/0011* (2013.01); *C07J 1/0022* (2013.01); *C07J 1/0037* (2013.01); *C07J 1/0048* (2013.01); *C07J 7/002* (2013.01); *G01N 2030/062* (2013.01)

(56) References Cited

FOREIGN PATENT DOCUMENTS

| CN | 103995068 A | 8/2014 |
|---|---|---|
| CN | 106526042 A | 3/2017 |
| CN | 107290460 A | 10/2017 |
| CN | 110132707 A | 8/2019 |
| JP | 2007248442 A | 9/2007 |

OTHER PUBLICATIONS

Shi, Jiang-hong et al.—CN 102183606 A machine translation—Sep. 14, 2011 (Year: 2011).*
Tan, Fang et al.—CN 103995068 A machine translation—Aug. 20, 2014 (Year: 2014).*
Xiao, Rui-Yang et al.—CN 106526042 A machine translation—Mar. 22, 2017 (Year: 2017).*
Nie, Yafeng, et al. "Determination of endocrine-disrupting chemicals in the liquid and solid phases of activated sludge by solid phase extraction and gas chromatography-mass spectrometry." Journal of Chromatography A 1216.42 (2009): 7071-7080. (Year: 2009).*
Yu, Yiyi, et al. "Determination of pharmaceuticals, steroid hormones, and endocrine-disrupting personal care products in sewage sludge by ultra-high-performance liquid chromatography-tandem mass spectrometry." Analytical and bioanalytical chemistry 399 (2011): 891-902. (Year: 2011).*

* cited by examiner

ULTRASONIC-ASSISTED PRETREATMENT METHOD FOR EXTRACTION OF MULTIPLE STEROID HORMONES IN SEDIMENT

TECHNICAL FIELD

The disclosure relates to an ultrasonic-assisted pretreatment method for extraction of multiple steroid hormones in a sediment, belonging to the field of analysis of trace level emerging contaminants in sediments.

BACKGROUND

Endocrine-disrupting chemicals (EDCs), belonging to a category of trace level emerging contaminants have become a hotspot in the field of environmental research at home and abroad in recent years. Steroid hormones are among the most potent endocrine disrupting chemicals. Although the detected concentrations in the environment are only at the ppt-ppb level, steroid hormones at this concentration level can still elicit significant endocrine-disrupting effects in aquatic organisms and amphibians, interfering with their growth, development and reproduction, and even causing more serious consequences such as skewness in gender distribution and decrease in population. The potential ecological and health risks of steroid hormones have attracted the attention of many countries. For example, the US Environmental Protection Agency has included 5 estrogens and 1 progestogen on the list of drinking water pollutant candidates. At present, China still has no corresponding regulations on steroid hormones in aquatic environment quality requirements, drinking water standards and the like, and related risk assessments and toxicological studies are underway. Accurately determining and reporting the concentrations of steroid hormones in various environmental media is the basis for such a series of studies, and the analysis and quantification of steroids in sediments and other complex environmental media is more challenging, so it is of great significance to establish a method with high recovery and good operability for extracting and quantifying steroid hormones in sediments.

At present, extraction methods of trace organic pollutants in sediments include Soxhlet extraction, accelerated solvent extraction, microwave-assisted extraction and ultrasonic-assisted extraction. The Soxhlet extraction is a classic extraction method that needs to consume lots of solvents and time, and the procedures are complex. The accelerated solvent extraction can greatly shorten the extraction time and reduce the consumption of solvents, but it needs expensive instruments, and high maintenance cost for the instrument components. The microwave-assisted extraction uses a small amount of solvents, but needs to consume much time and manpower. In the accelerated solvent extraction and the microwave assisted extraction, samples are extracted under high temperature and high pressure, thereby sometimes causing the decomposition of target pollutants and thus reducing the recovery. In view of this, the ultrasonic-assisted extraction is more suitable for extracting steroid hormones in sediments, and in this disclosure, some key parameters and conditions are optimized to improve the recovery of extraction and the accuracy of detection.

SUMMARY

The disclosure provides an ultrasonic-assisted extraction method as pretreatment for quantification of multiple steroid hormones in a sediment. By selecting extractants from the combinations of two of methanol, acetonitrile and acetone, the method has the advantages of simple procedures, small amount of organic impurities in the extract, little interference and wide application, and can effectively enhance the recovery and accuracy of steroid hormone detection.

The disclosure discloses an ultrasonic assisted extraction method of multiple steroid hormones in a sediment. The steroid hormones are extracted three times by ultrasonic-assisted extraction. Extractants for the three times of extraction are two of methanol, acetonitrile and acetone, and the steroid hormones include estrogens, androgens, and progestogens.

In one embodiment of the disclosure, solvents for the three times of extraction are respectively 5 mL of methanol, 5 mL of acetonitrile and 5 mL of acetonitrile.

In one embodiment of the disclosure, solvents for the three times of extraction are respectively 5 mL of methanol, 5 mL of methanol and 5 mL of acetone.

In one embodiment of the disclosure, solvents for the three times of extraction are respectively 5 mL of methanol, 5 mL of acetone and 5 mL of acetone.

The pretreatment method of ultrasonic-assisted extraction of multiple steroid hormones in a sediment disclosed by the disclosure specifically includes the following steps:

(1) lyophilizing the sediment, grinding the sediment, and passing the ground sediment through a 40-60-mesh sieve to obtain a sample;

(2) placing the sample obtained in the first step in a container;

(3) adding an extractant to the container in the second step, completely mixing the content by vortex for 15 s-30 s, centrifuging the mixture to collect the supernatant after ultrasonication, and performing extraction three times; and (4) after combining the supernatants of the three times of extraction obtained in the third step, concentrating the mixture under nitrogen flow at 20-30° C., and passing the concentrated mixture through a filter.

In one embodiment of the disclosure, step (1) is to pre-freeze the sediment at −60-−80° C. overnight and lyophilize the sediment at −45° C.

In one embodiment of the disclosure, in step (2), an amount of the sample placed in the container is 0.5-5.0 g.

In one embodiment of the disclosure, in step (2), the container is made of polytetrafluoroethylene.

In one embodiment of the disclosure, in step (3), a volume of the extractant is 5-10 mL, the number of times of extraction is 3, and an extraction time is 10-15 min.

In one embodiment of the disclosure, in step (3), a frequency of an ultrasonic cleaner is set to 40-60 kHz.

In one embodiment of the disclosure, in step (3), a centrifugation time after the three times of extraction is 15-30 min.

In one embodiment of the disclosure, in step (4), the mixture is concentrated under nitrogen flow to a volume of 1 mL, and a pore size of the filter is 0.22 μm.

The disclosure discloses application of the pretreatment method in the field of environmental studies.

The disclosure discloses a method for quantification of steroid hormones in a sediment or sandy soil. The method includes treating a sample by using the above pretreatment method, and then analyzing the extract by ultra-performance liquid chromatography-tandem mass spectrometry to quantification of the steroid hormones in the sample. The steroid hormones include estrogens, androgens, and progestogens. The sample is the sediment or sandy soil.

In one embodiment of the disclosure, conditions for the liquid chromatography when analyzing the estrogens are: a mobile phase A is 0.05% ammonia water, a mobile phase B is acetonitrile, a flow rate is 0.2 mL/min, an injection volume is 5 µL, and a column temperature is 40° C. Conditions for elution are: at 0-0.25 min, the mobile phase is 70% mobile phase A+30% mobile phase B; at 0.25-3 min, the mobile phase B is gradually increased to 90%, and the condition is held for 2 min; and then, the column is immediately restored to the initial mobile phase, namely 70% mobile phase A+30% mobile phase B, and the condition is held for 1 min.

In one embodiment of the disclosure, conditions for the mass spectrometry when analyzing the estrogens are: electrospray ionization is used in negative ion mode (ESI⁻); a scanning mode is multiselected reaction monitoring (MRM); a capillary voltage is 2.5 kV; a cone voltage and an extractor voltage are respectively 30.0 V and 3.0 V; an ion source temperature and a desolvation temperature are respectively 150° C. and 350° C.; a cone gas flow and a desolvation gas flow are respectively 50 L/hr and 700 L/hr; and a collision gas flow is 0.16 mL/min.

In one embodiment of the disclosure, conditions for the chromatography when analyzing the androgens and the progestogens are: a mobile phase A is a methanol solution containing 0.1% of formic acid, a volume ratio of water to methanol in the methanol solution is 98:2, a mobile phase B is acetonitrile, a flow rate is 0.4 mL/min, an injection volume is 5 µL, and a column temperature is 40° C. Conditions for elution are: at 0-0.25 min, the mobile phase is 90% mobile phase A+10% mobile phase B; at 0.25-1 min, the mobile phase B is gradually increased to 70%; at 1-3 min, the mobile phase B is increased to 95%, and the condition is held for 1 min; and then, the column is immediately restored to the initial mobile phase, namely 90% mobile phase A+10% mobile phase B, and the condition is held for 1 min.

In one embodiment of the disclosure, when detecting the androgens and the progestogens, electrospray ionization is used in positive ion mode (ESI⁺), and a scanning mode is multiselected reaction monitoring (MRM). Conditions for the mass spectrometry are: a capillary voltage is 3.0 kV; a cone voltage and an extractor voltage are respectively 30.0 V and 3.0 V; an ion source temperature and a desolvation temperature are respectively 150° C. and 500° C.; a cone gas flow and a desolvation gas flow are respectively 50 L/hr and 900 L/hr; and a collision gas flow is 0.16 mL/min.

In one embodiment of the disclosure, the steroid hormones include one or more of estrone, estradiol, ethinylestradiol, androstenedione, testosterone, methyltestosterone, levonorgestrel and progesterone.

The disclosure has the following beneficial effects:

1. By using the method of the disclosure, the maximum recovery can be up to 100%. The application range is wide, and a recovery of the plurality of steroid hormones each can be up to 73%.

2. According to the disclosure, the steroid hormones in the sediment are extracted by using organic solvents assisted by ultrasound, so the method is simple to operate. Compared with the Soxhlet extraction, the extraction time is greatly shortened, and the amount of extraction solvents is reduced. Compared with the accelerated solvent extraction, the requirements for instruments and equipment are not high, and the maintenance cost is lower.

3. According to the disclosure, the extraction is performed under normal temperature and normal pressure, so the possible decomposition of target analytes under high temperature and high pressure is avoided, which is beneficial to enhancing the recovery and accuracy.

4. According to the Soxhlet extraction and the extraction methods under high temperature and high pressure conditions, humic acids and other organic matters in the sediment are usually extracted together with the steroid hormones, which enhances the background noises during detection and increases interference for analysis and detection. According to the disclosure, the amount of organic impurities in the extraction product is small, and the interference is little.

5. According to the disclosure, the polytetrafluoroethylene is used instead of the commonly used plastic or glass container, which reduces the adsorption of the container wall and is beneficial to enhancing the recovery.

DETAILED DESCRIPTION

Figure 1:
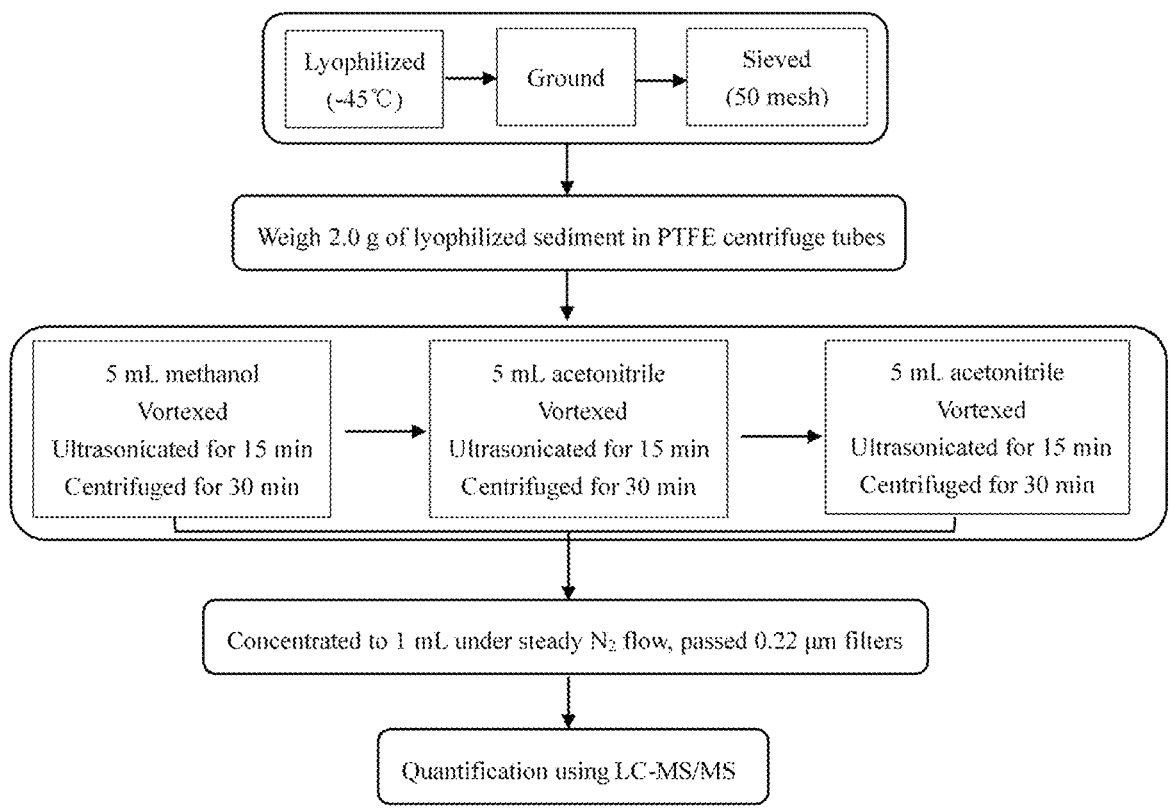
FIG. 1 is a flow chart of ultrasonic-assisted extraction of multiple steroid hormones in a sediment.

Embodiments of the disclosure will be described below with specific examples.

The disclosure discloses an ultrasonic-assisted pretreatment method for extraction of multiple residual steroid hormones in a sediment, which can be used to extract 8 steroid hormones such as estrogens, androgens and progestogens in the sediment. The method uses the following instruments and reagents:

Instruments: ultrasonic instrument (Ningbo Scientz Biotechnology Co., Ltd., SB-500DTY); lyophilizer (LABCONCO); centrifuge (Eppendorf, Centrifuge 5804 R); vortex shaker (Shanghai Huxi Analysis Instrument Factory Co., Ltd., WH-1 Mini Vortex Mixer); nitrogen purging device (Reeko Instrument USA, AUTO SPE-06D); and high performance liquid chromatography-tandem mass spectrometry (Waters, ACQUITY UPLC Xevo TQ), Waters ACQUITY UPLC R BEH C18 (100 mm×2.1 mm×1.7 µm).

Reagents: the extraction solvents include methanol, acetonitrile and acetone, all of which are of HPLC grade (Merck, Germany), and ultrapure water.

The test method of the recovery is as follows:

100 µL of a mixed standard solution of steroid hormones with a concentration of 1 mg/L is added to the sediment or sandy soil, that is, the spiking amount is 100 ng. At the same time, unspiked blanks are prepared. Two duplicate samples are prepared for each experimental group. After 2 hours of standing, extraction and detection are performed, and the recovery is calculated according to the following formula:

$$R = \frac{M - M_0}{100} \times 100\%$$

where R is the recovery, %; M is the detected amount of the spiked sample, ng; and Mo is the detected amount of the blank sample, ng.

Example 1: Establishment of Standard Curves (1) Firstly, each steroid hormone standard was accurately prepared into a single-solute standard stock solution with a concentration of 1 g/L, the single-solute standard stock solutions were respectively diluted into 1 mg/L standard samples, and the standard samples were subjected to LC-MS/MS analysis to determine the respective retention times.

Conditions for the liquid chromatography when analyzing the estrogens were: a mobile phase A was 0.05% ammonia water, a mobile phase B was acetonitrile, a flow rate was 0.2 mL/min, an injection volume was 5 μL, and a column temperature was 40° C. Conditions for elution were: at 0-0.25 min, the mobile phase was 70% phase A+30% phase B; at 0.25-3 min, the phase B was gradually increased to 90%, and the condition was held for 2 min; and then, the column was immediately restored to the initial mobile phase, namely 70% phase A+30% phase B, and the condition was held for 1 min.

Conditions for the mass spectrometry were: electrospray ionization was used in negative ion mode (ESI⁻); a scanning mode was multiselected reaction monitoring (MRM); a capillary voltage was 2.5 kV; a cone voltage and an extractor voltage were respectively 30.0 V and 3.0 V; an ion source temperature and a desolvation temperature were respectively 150° C. and 350° C.; a cone gas flow and a desolvation gas flow were respectively 50 L/hr and 700 L/hr; and a collision gas flow was 0.16 mL/min.

Conditions for the chromatography when analyzing the androgens and the progestogens were: a mobile phase A was a methanol solution containing 0.1% of formic acid (a ratio of water to methanol was 98:2, v/v), a mobile phase B was acetonitrile, a flow rate was 0.4 mL/min, an injection volume was 5 μL, and a column temperature was 40° C. Conditions for elution were: at 0-0.25 min, the mobile phase was 90% phase A+10% phase B; at 0.25-1 min, the phase B was gradually increased to 70%; at 1-3 min, the phase B was increased to 95%, and the condition was held for 1 min; and then, the column was immediately restored to the initial mobile phase, namely 90% phase A+10% phase B, and the condition was held for 1 min.

Conditions for the mass spectrometry were: when detecting the androgens and the progestogens, electrospray ionization is used in positive ion mode (ESI⁺); a scanning mode was multiselected reaction monitoring (MRM); a capillary voltage was 3.0 kV; a cone voltage and an extractor voltage were respectively 30.0 V and 3.0 V; an ion source temperature and a desolvation temperature were respectively 150° C. and 500° C.; a cone gas flow and a desolvation gas flow were respectively 50 L/hr and 900 L/hr; and a collision gas flow was 0.16 mL/min.

(2) Then, mixed standard stock solutions of steroid hormones with a concentration of 10 mg/L were prepared, and diluted into a series of mixed standard solutions with concentrations of 0.5 μg/L, 2 μg/L, 5 μg/L, 20 μg/L, 50 μg/L and 200 μg/L respectively. The concentrations of the steroid hormones in the mixed standard solutions were uniform. Finally, by taking a nominal injection concentration as the abscissa X (μg/L) and a peak area as the ordinate Y, the standard curves and detection limits of corresponding steroid hormones were obtained. The results are shown in Table 1.

TABLE 1

| Steroid hormone | Retention time (min) | Standard curve | Degree of fitting ($R^2$) | Limit of quantitation (ppb) | Linear range (ppb) |
|---|---|---|---|---|---|
| Estrone E1 | 3.29 | Y = 308.994X − 19.467 | 0.9980 | 0.292 | 0.5-200 |
| Estradiol E2 | 3.02 | Y = 52.486X − 7.115 | 0.9984 | 0.381 | 0.5-200 |
| Ethinylestradiol EE2 | 3.17 | Y = 40.920X − 6.289 | 0.9960 | 0.710 | 0.5-200 |
| Androstenedione AND | 1.88 | Y = 1712.42X − 239.601 | 0.9933 | 0.110 | 0.5-200 |
| Testosterone TES | 1.80 | Y = 1366.26X − 132.456 | 0.9967 | 0.222 | 0.5-200 |
| Methyltestosterone MET | 1.87 | Y = 1130.24X + 42.805 | 0.9981 | 0.147 | 0.5-200 |
| Levonorgestrel LEV | 1.93 | Y = 93.07X − 15.607 | 0.9933 | 0.444 | 2.0-200 |
| Progesterone PRO | 2.21 | Y = 1894.85X − 40.546 | 0.9968 | 0.270 | 0.5-200 |

Example 2: An Ultrasonic-Assisted Pretreatment Method Tor Extraction of Multiple Steroid Hormones in Sediment As shown in FIG. 1, a collected sediment was uniformly spread on a glass petri dish with a thickness of not more than 5 mm. The sediment was placed in a −80° C. refrigerator overnight. The sediment was taken out the next day, immediately placed in a lyophilizer and lyophilized. After 16-24 hours, the sediment was taken out, ground in a mortar, and passed through a 50-mesh sieve for later extraction. The sample that could not be subjected to extraction immediately was wrapped with aluminum foil, sealed in a sealing bag, and stored in a −20° C. refrigerator.

2.0 g of the lyophilized and ground sediment was accurately weighed, and placed in a 50 mL polytetrafluoroethylene centrifuge tube. 5 mL of methanol was added. After the centrifuge tube was well capped, the mixture was mixed thoroughly with a vortex shaker, subjected to ultrasonic extraction under the conditions of 20° C. and 59 kHz for 15 min, and then centrifuged in a centrifuge at 4000 rpm for 30 min for solid-liquid separation. The supernatant was sucked out with a glass pipette and put in a glass nitrogen purging tube. The above steps are repeated 2 times, but the extraction solvent was changed to 5 mL of acetonitrile. When mixing with the vortex shaker, it must be ensured that the sediment after centrifugal separation could be fully resuspended in the extractant without lumpy solids. About 15 mL of the supernatant after three times of centrifugation was collected in a nitrogen purging tube, concentrated to 1 mL under a steady nitrogen flow, passed through a 0.22-μm PTFE filter, and stored in an amber autosampler vial for detection.

The extract was analyzed by high performance liquid chromatography-tandem mass spectrometry (LC-MS/MS). Conditions for the liquid chromatography when analyzing the estrogens were: a mobile phase A was 0.05% ammonia water, a mobile phase B was acetonitrile, a flow rate was 0.2 mL/min, an injection volume was 5 μL, and a column temperature was 40° C. Conditions for elution were: at 0-0.25 min, the mobile phase was 70% phase A+30% phase B; at 0.25-3 min, the phase B was gradually increased to 90%, and the condition was held for 2 min; and then, the column was immediately restored to the initial mobile phase, namely 70% phase A+30% phase B, and the condition was held for 1 min. Conditions for the mass spectrometry were: electrospray ionization was used in negative ion mode (ESI$^-$); a scanning mode was multiselected reaction monitoring (MRM); a capillary voltage was 2.5 kV; a cone voltage and an extractor voltage were respectively 30.0 V and 3.0 V; an ion source temperature and a desolvation temperature were respectively 150° C. and 350° C.; a cone gas flow and a desolvation gas flow were respectively 50 L/hr and 700 L/hr; and a collision gas flow was 0.16 mL/min. Conditions for the chromatography when analyzing the androgens and the progestogens were: a mobile phase A was a methanol solution containing 0.1% of formic acid (a ratio of water to methanol was 98:2, v/v), a mobile phase B was acetonitrile, a flow rate was 0.4 mL/min, an injection volume was 5 μL, and a column temperature was 40° C. Conditions for elution were: at 0-0.25 min, the mobile phase was 90% phase A+10% phase B; at 0.25-1 min, the phase B was gradually increased to 70%; at 1-3 min, the phase B was increased to 95%, and the condition was held for 1 min; and then, the column was immediately restored to the initial mobile phase, namely 90% phase A+10% phase B, and the condition was held for 1 min. Conditions for the mass spectrometry were: when detecting the androgens and the progestogens, electrospray ionization was used in positive ion mode (ESI$^+$); a scanning mode was multiselected reaction monitoring (MRM); a capillary voltage was 3.0 kV; a cone voltage and an extractor voltage were respectively 30.0 V and 3.0 V; an ion source temperature and a desolvation temperature were respectively 150° C. and 500° C.; a cone gas flow and a desolvation gas flow were respectively 50 L/hr and 900 L/hr; and a collision gas flow was 0.16 mL/min.

Example 3: Pretreatment Method for Ultrasonic Assisted Extraction of Multiple Steroid Hormones in Sandy Soil Sandy soil was placed on a glass petri dish with a thickness of not more than 5 mm. The sandy soil was placed in a −80° C. refrigerator overnight. The sediment was taken out the next day, immediately placed in a lyophilizer and lyophilized. After 16-24 hours, the sandy soil was taken out, ground in a mortar, and passed through a 50-mesh sieve for later extraction.

2.0 g of the lyophilized sandy soil was accurately weighed, and placed in a 50 mL polytetrafluoroethylene centrifuge tube. 5 mL of methanol was added. After the centrifuge tube was well capped, the mixture was mixed thoroughly with a vortex shaker, subjected to ultrasonic extraction under the conditions of 30° C. and 59 kHz for 15 min, and then centrifuged in a centrifuge at 4000 rpm for 30 min for solid-liquid separation. The supernatant was sucked out with a glass pipette and put in a glass nitrogen purging tube. The above steps are repeated 2 times, but the extraction solvent was changed to 5 mL of acetonitrile. When mixing with the vortex shaker, it must be ensured that the sediment after centrifugal separation could be fully resuspended in the extractant without lumpy solids. About 15 mL of the supernatant after three times of centrifugation was collected in a nitrogen purging tube, concentrated to 1 mL under a steady nitrogen flow, passed through a 0.22-μm PTFE filter, and stored in an amber autosampler vial for detection.

The extract was analyzed by high performance liquid chromatography-tandem mass spectrometry (LC-MS/MS). Conditions for the liquid chromatography when analyzing the estrogens were: a mobile phase A was 0.05% ammonia water, a mobile phase B was acetonitrile, a flow rate was 0.2 mL/min, an injection volume was 5 μL, and a column temperature was 40° C. Conditions for elution were: at 0-0.25 min, the mobile phase was 70% phase A+30% phase B; at 0.25-3 min, the phase B was gradually increased to 90%, and the condition was held for 2 min; and then, the column was immediately restored to the initial mobile phase, namely 70% phase A+30% phase B, and the condition was held for 1 min. Conditions for the mass spectrometry were: electrospray ionization was used in negative ion mode (ESI$^-$); a scanning mode was multiselected reaction monitoring (MRM); a capillary voltage was 2.5 kV; a cone voltage and an extractor voltage were respectively 30.0 V and 3.0 V; an ion source temperature and a desolvation temperature were respectively 150° C. and 350° C.; a cone gas flow and a desolvation gas flow were respectively 50 L/hr and 700 L/hr; and a collision gas flow was 0.16 mL/min. Conditions for the chromatography when analyzing the androgens and the progestogens were: a mobile phase A was a methanol solution containing 0.1% of formic acid (a ratio of water to methanol was 98:2, v/v), a mobile phase B was acetonitrile, a flow rate was 0.4 mL/min, an injection volume was 5 μL, and a column temperature was 40° C. Conditions for elution were: at 0-0.25 min, the mobile phase was 90% phase A+10% phase B; at 0.25-1 min, the phase B was gradually increased to 70%; at 1-3 min, the phase B was increased to 95%, and the condition was held for 1 min; and then, the column was immediately restored to the initial mobile phase, namely 90% phase A+10% phase B, and the condition was held for 1 min. Conditions for the mass spectrometry were: when detecting the androgens and the progestogens, electrospray ionization was used in positive ion mode (ESI$^+$); a scanning mode was multiselected reaction monitoring (MRM); a capillary voltage was 3.0 kV; a cone voltage and an extractor voltage were respectively 30.0 V and 3.0 V; an ion source temperature and a desolvation temperature were respectively 150° C. and 500° C.; a cone gas flow and a desolvation gas flow were respectively 50 L/hr and 900 L/hr; and a collision gas flow was 0.16 mL/min.

Example 4

Figure 2:
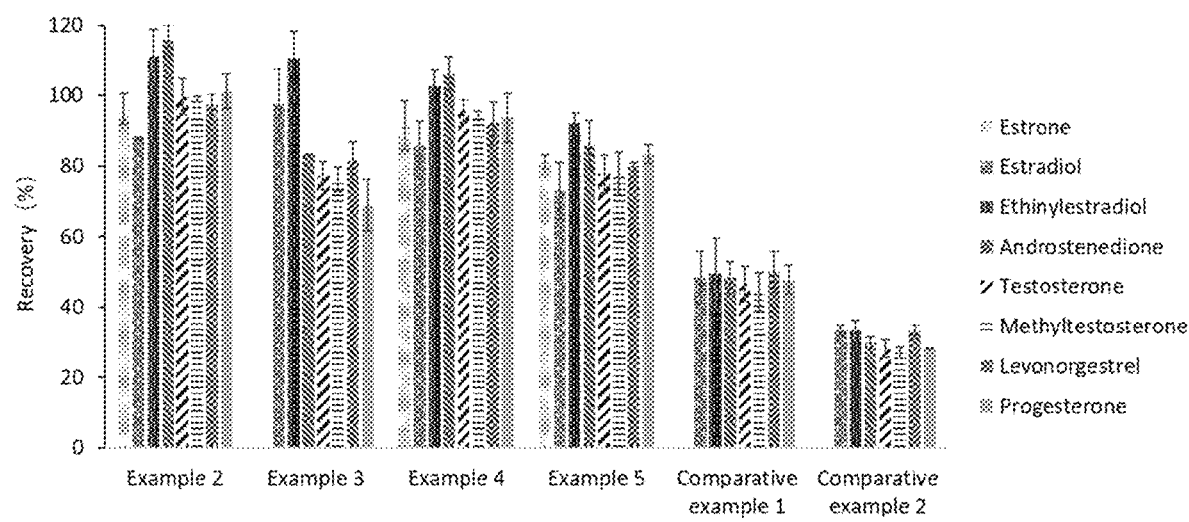
FIG. 2 is a diagram of recoveries of steroid hormones by using different extractant combinations, where E1 is estrone, E2 is estradiol (17β-estradiol), EE2 is ethinylestradiol, AND is androstenedione, TES is testosterone, MET is methyltestosterone (17α-methyltestosterone), LEV is levonorgestrel, and PRO is progesterone.

The solvent for the second extraction was changed to methanol, and the solvent for the third extraction was changed to acetone. The rest of the operations and steps were the same as in Example 2. That is, 5 mL of methanol, 5 mL of methanol and 5 mL of acetone were sequentially used for ultrasonic-assisted extraction of steroid hormones in the sediment. The results are shown in Table 2 and FIG. 2. The recoveries of the steroid hormones are 86%-106%.

Example 5

The solvent for the second extraction and the third extraction was changed to acetone. The rest of the operations and steps were the same as in Example 2. That is, 5 mL of methanol, 5 mL of acetone and 5 mL of acetone were sequentially used for ultrasonic-assisted extraction of steroid hormones in the sediment. The results are shown in Table 2 and FIG. 2. The recoveries of the steroid hormones are 73%-92%.

Example 6: Accuracy of Method

Recovery test: the sediment or sandy soil was spiked with 100 μL of a mixed standard solution of steroid hormones with each compound at 1 mg/L was added to the sediment or sandy soil, that is, the spiking amount was 100 ng. At the same time, unspiked blanks were prepared. Two duplicate samples were prepared for each experimental group. After 2 hours of standing, extraction and detection were performed, and the recovery of the method was calculated. The specific results are shown in Table 2.

Comparative Example 1

The solvent for the three times of extraction was changed to methanol, and the rest of operations and steps were the same as in Example 2. The results are shown in Table 2 and FIG. 2. The recoveries of the steroid hormones are 44%-50%, which are significantly lower than the recoveries 88%-116% in Example 2. When 5 mL of methanol is used for the three times of ultrasonic-assisted extraction on the steroid hormones in the sediment, the effect is not as good as that of the solvent combination of 5 mL of methanol, 5 mL of acetonitrile and 5 mL of acetonitrile, indicating that the recovery of extraction with one extractant is not as good as that of two extractants.

Comparative Example 2

After the supernatant obtained after the three times of extraction was concentrated to obtain 1 mL of sample, 250 mL of ultrapure water was added and completely mixed. Then, the mixture was passed at a flow rate of 10 mL/min through an Oasis HLB solid-phase extraction column (Waters, 6 cc, 500 mg) sequentially activated with 5 mL of methanol and 5 mL of ultrapure water. After the completion of the sample loading, impurities in the column were washed off with a 5% methanol solution, and the HLB column was blow-dried with nitrogen for 20 min. Then, the target analyte was sequentially eluted with 7 mL of methanol and 7 mL of a methanol-acetone solution (1:1, v/v), finally concentrated to 1 mL under a steady nitrogen flow, and stored in an amber autosampler vial for detection. The rest of operations and steps were the same as in Example 2. The results are shown in Table 2 and FIG. 2. The recoveries of the steroid hormones are 27%-33%, which are significantly lower than those in Example 2, indicating that the additional SPE cleaning step will result in a decrease in the recovery.

TABLE 2

Influence of different pretreatment methods on recoveries of steroid hormones

| Recovery/% | Example 2 | Example 3 | Example 4 | Example 5 | Comparative example 1 | Comparative example 2 |
|---|---|---|---|---|---|---|
| Estrone | 96 | — | 92 | 81 | — | — |
| Estradiol | 88 | 98 | 86 | 73 | 48 | 33 |
| Ethinylestradiol | 111 | 110 | 103 | 92 | 49 | 33 |
| Androstenedione | 116 | 83 | 106 | 86 | 48 | 30 |
| Testosterone | 100 | 77 | 96 | 78 | 46 | 28 |
| Methyltestosterone | 99 | 76 | 94 | 78 | 44 | 27 |
| Levonorgestrel | 97 | 82 | 92 | 80 | 50 | 33 |
| Progesterone | 101 | 69 | 94 | 83 | 48 | 28 |

Note:
Due to the lack of experimental standards, the recoveries of E1 in Example 2, Comparative examples 1 and 2 were not available in the disclosure.

What is claimed is:

1. A pretreatment method for extraction of multiple steroid hormones in a sediment, comprising the following steps:
   (1) lyophilizing the sediment, and grinding the sediment to 40-60 mesh;
   (2) placing a sample obtained in step (1) in a container;
   (3) adding an extractant to the container in step (2) for extraction, shaking a mixture for 15-30 s, ultrasonicating the mixture, centrifuging the mixture to collect a supernatant after ultrasonication, and repeating the extraction three times; and
   (4) after mixing the supernatants of the three times of extraction obtained in step (3), concentrating the mixture under a nitrogen flow at 20-30° C., and passing the concentrated mixture through a filter;
   wherein in the step (1), the lyophilizing is to pre-freeze the sediment at −60 to −80° C. overnight and lyophilize the sediment at −45° C.;
   wherein solvents for the three times of extraction are methanol, acetonitrile and acetonitrile, respectively, or methanol, methanol and acetone, respectively, or methanol, acetone and acetone, respectively; and the pretreatment method does not need an SPE cleaning step.

2. The pretreatment method according to claim 1, wherein the steroid hormones comprise estrogens, androgens, and progestogens.

3. The pretreatment method according to claim 1, wherein in the step (2), an amount of the sample placed in the container is 0.5-5.0 g.

4. The pretreatment method according to claim 1, wherein in the step (2), the container is made of a polytetrafluoroethylene material.

5. The pretreatment method according to claim 3, wherein in the step (3), a volume of the extractant is 5-10 mL.

6. The pretreatment method according to claim 1, wherein in the step (3), a frequency of ultrasound in the ultrasonication is 45-60 kHz.

7. A method for detecting a content of steroid hormones in a sediment or sandy soil, comprising: treating a sample by using the pretreatment method according to claim 1 to extract the steroid hormones in the sample; and then analyzing the sample obtained by the extraction by high performance liquid chromatography-tandem mass spectrometry to quantitatively detect the content of the steroid hormones in the sample, wherein the steroid hormones comprise estrogens, androgens and progestogens; and the sample is the sediment or sandy soil.

8. The method according to claim 7, wherein conditions for the liquid chromatography when analyzing the estrogens are that: a mobile phase A is 0.05% ammonia water, a mobile phase B is acetonitrile, a flow rate is 0.2 mL/min, an injection volume is 5 μL, and a column temperature is 40° C.; and conditions for elution are that: at 0-0.25 min, a mobile phase is 70% mobile phase A +30% mobile phase B; at 0.25-3 min, the mobile phase B is gradually increased to 90%, and a condition is held for 2 min; and then, a column is immediately restored to an initial mobile phase, namely 70% mobile phase A +30% mobile phase B, and a condition is held for 1 min.

9. The method according to claim 8, wherein conditions for the mass spectrometry when analyzing the estrogens are that: electrospray ionization is used in negative ion mode (ESI$^-$); a scanning mode is multiselected reaction monitoring (MRM); a capillary voltage is 2.5 kV; a cone voltage and an extractor voltage are 30.0 V and 3.0 V, respectively; an ion source temperature and a desolvation temperature are 150° C. and 350° C., respectively; a cone gas flow and a desolvation gas flow are 50 L/hr and 700 L/hr, respectively; and a collision gas flow is 0.16 mL/min.

10. The method according to claim 7, wherein conditions for the chromatography when analyzing the androgens and the progestogens are that: a mobile phase A is a methanol solution containing 0.1% of formic acid, a volume ratio of water to methanol in the methanol solution is 98:2, a mobile phase B is acetonitrile, a flow rate is 0.4 mL/min, an injection volume is 5 μL, and a column temperature is 40° C.; and conditions for elution are that: at 0-0.25 min, a mobile phase is 90% mobile phase A +10% mobile phase B; at 0.25-1 min, the mobile phase B is gradually increased to 70%; at 1-3 min, the mobile phase B is increased to 95%, and a condition is held for 1 min; and then, a column is immediately restored to an initial mobile phase, namely 90% mobile phase A +10% mobile phase B, and a condition is held for 1 min.

11. The method according to claim 10, wherein when detecting the androgens and the progestogens, electrospray ionization is used in positive ion mode (ESI$^+$), and a scanning mode is multiselected reaction monitoring (MRM).

12. The method according to claim 11, wherein conditions for the mass spectrometry are that: a capillary voltage is 3.0 kV; a cone voltage and an extractor voltage are 30.0 V and 3.0 V, respectively; an ion source temperature and a desolvation temperature are 150° C. and 500° C., respectively; a cone gas flow and a desolvation gas flow are 50 L/hr and 900 L/hr, respectively; and a collision gas flow is 0.16 mL/min.

13. The method according to claim 7, wherein the steroid hormones comprise one or more of estrone, estradiol, ethinylestradiol, androstenedione, testosterone, methyltestosterone, levonorgestrel and progesterone.

* * * * *